(12) United States Patent
Chaudhari et al.

(10) Patent No.: US 7,022,871 B2
(45) Date of Patent: Apr. 4, 2006

(54) PROCESS FOR THE SYNTHESIS OF POLYCARBAMATES

(75) Inventors: Raghunath Vitthal Chaudhari, Pune (IN); Ashutosh Anant Kelkar, Pune (IN); Sunil Purushottam Gupte, Pune (IN); Sunil Sadashiv Divekar, Pune (IN); Subramanian Ganapathy, Pune (IN)

(73) Assignee: Huntsman International LLC, Salt Lake City, UT (US)

( * ) Notice: Subject to any disclaimer, the term of this patent is extended or adjusted under 35 U.S.C. 154(b) by 0 days.

(21) Appl. No.: 10/180,442

(22) Filed: Jun. 26, 2002

(65) Prior Publication Data

US 2003/0135009 A1 Jul. 17, 2003

Related U.S. Application Data

(63) Continuation of application No. PCT/US00/34103, filed on Dec. 14, 2000.

(30) Foreign Application Priority Data

Dec. 27, 1999 (IN) .......... 960/99

(51) Int. Cl.
*C07C 269/00* (2006.01)
(52) U.S. Cl. .......... 560/25
(58) Field of Classification Search .......... 560/25
See application file for complete search history.

(56) References Cited

U.S. PATENT DOCUMENTS

| 4,230,877 A | 10/1980 | Shawl et al. |
| 4,242,520 A | 12/1980 | Moy |
| 4,260,781 A | 4/1981 | Harvey |
| 4,319,018 A | 3/1982 | Miyata et al. |
| 4,375,000 A | 2/1983 | Merger et al. |
| 4,552,974 A | 11/1985 | Fukuoka et al. |
| 4,621,149 A * | 11/1986 | Fukuoka et al. .......... 560/24 |
| 4,694,097 A | 9/1987 | Alper et al. |
| 5,194,660 A | 3/1993 | Leung et al. |
| 5,502,241 A | 3/1996 | Chaudhari et al. |

FOREIGN PATENT DOCUMENTS

| EP | 0 083 096 | 7/1983 |
| EP | 0 359 519 | 3/1990 |
| GB | 2 054 584 | 2/1981 |
| GB | WO 98/55450 A1 * | 12/1998 |
| JP | 56012357 | 2/1981 |

OTHER PUBLICATIONS

S. Kanagasabapathy, et al.., "Oxidative Carbonylation of Aniline Over Pd-ZSM-5 Catalyst", Catalysis Letters 25 (1994), pp. 361-364, J.C. Baltzer AG, Science Publishers.
V.L.K. Valli, et al., "Oxidative Carbonylation of Aliphatic Mono-, Di-, and Triamines Catalyzed by Montmorillonite-Bipyridinylpalladium (II) Acetate", Organometallics 1995, 14, pp. 80-82, American Chemical Society.

* cited by examiner

*Primary Examiner*—Paul A. Zucker
(74) *Attorney, Agent, or Firm*—Nicole Graham

(57) ABSTRACT

Process for the synthesis of polyurethane derivatives from aromatic polyamine compounds. The method involves the reaction of an aromatic polyamine compound with CO and $O_2$ in the presence of a catalyst comprising a Group VIII or lanthanide metal on a solid support and a halogenide promoter.

34 Claims, No Drawings

PROCESS FOR THE SYNTHESIS OF POLYCARBAMATES

CROSS REFERENCE TO RELATED APPLICATIONS

This application is a continuation of international application PCT US00/34103, filed Dec. 14, 2000.

FIELD OF INVENTION

This invention relates to a method for the preparation of polymeric carbamates by oxidative carbonylation of polymeric amino compounds. More particularly, it relates to an industrially advantageous method of producing polymeric MDU (methylene diphenyl diurethane) in high selectivity by a direct carbonylation method. This route provides a non-phosgene method for the preparation of polymeric carbamates.

BACKGROUND OF THE INVENTION

Conventionally, aromatic diisocyanates are prepared by phosgenation of the corresponding diamino compounds. The use of phosgene results in the generation of hydrochloric acid as a side product, which is the cause of severe corrosion. Considering the environmental hazard and corrosion problems in the phosgenation route, it is important to develop a route without using phosgene.

MDI is an important starting material for the production of polyurethanes that are useful as elastomers, artificial leather, coatings, spandex fibers etc. Diphenyl methane dicarbamates are useful precursors for the preparation of diphenylmethane diisocyanates (MDI).

Various methods for the preparation of alkyl and aromatic carbamates by carbonylation of corresponding amino compounds with carbon monoxide and oxygen using Group VIII metal catalysts have been reported (U.S. Pat. Nos. 5,502,241; 5,194,660; 4,694,097 and 4,242,520; EP-A 83096).

Asahi Chemicals have proposed a process for the preparation of 4,4'-MDU (U.S. Pat. Nos. 4,552,974; 4,230,877; 4,319,018; GB-A 2054584; JP-A 12357/81) by condensation of ethyl N-phenyl carbamate with formaldehyde in the presence of acids, such as mineral acids or organic sulfonic acids. This requires relatively severe reaction conditions.

Recently, Valli and Alper have published a work on oxidative carbonylation of various aliphatic diamines to aliphatic diurethanes using Pd-clay/NaI catalyst system (Organomett. 14, 81 (1995)).

Oxidative carbonylation of aniline to the corresponding aromatic urethane has already been disclosed in Catalysis Letters (1994), 25, p. 361–364.

However, none of the prior art documents report catalytic conversion of polymeric amino compounds to their corresponding carbamate derivatives by a clean and environmentally benign route.

SUMMARY OF THE INVENTION

Therefore, the present invention is directed towards the catalytic conversion of polymeric amino compounds to their corresponding carbamate derivatives by a clean and environmentally benign route. More particularly, the present invention is concerned with the use of a catalytic route for the conversion of aromatic polyamino compounds to polycarbamates via oxidative carbonylation. Such a route eliminates the use of toxic phosgene and associated corrosion problems leading to an environmentally benign process.

DETAILED DESCRIPTION OF THE INVENTION

The present invention relates to a clean catalytic process for producing polymeric carbamate derivatives in a single step, wherein an aromatic polyamine reacts with carbon monoxide, oxygen and hydroxyl containing organic compounds in the presence of a transition metal catalyst and a halogenide an iodide promoter. Usually, the reaction is carried out in a liquid phase at 60 to 300° C. and pressures of 10 bar to 100 bar. The catalyst compositions described herein comprise a Group VIII metal (e.g. palladium, platinum, nickel, rhodium, ruthenium or cobalt) or a complex thereof, or a lanthanide metal, particularly cerium. They are used in combination with a halogenide, e.g. an iodide, source as promoter, as illustrated by various alkali metal iodides.

Any aromatic polyamine may be employed in the present invention, specifically polymeric DADPM (DiAmino DiPhenyl Methane). Other essential reagents in the method of this invention are an oxidising agent, such as oxygen, and carbon monoxide, which react with the polymeric amine and hydroxy compound to form the desired polymeric carbamate.

The end product formed in the present invention is the compound represented by formula I:

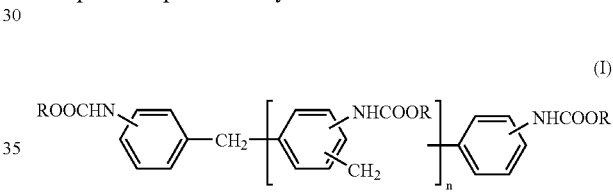

(I)

Wherein n is greater than 0, suitably 1–20, preferably 1–10; R is an alkyl group having 1–15 carbon atoms, preferably 1–6 carbon atoms, aromatic groups or an alicyclic group having 3–30 carbon atoms, preferably 5–10 carbon atoms. Preferred examples of R groups are methyl, ethyl, propyl (n- or iso-), butyl (n- or iso-), pentyl (n- and various isomers), hexyl (n- and various isomers), alicyclic groups such as cyclopentyl and cyclohexyl and aromatic groups such as phenyl, or halogenated phenyl.

Representative examples of the compound in the formula I includes polymeric dimethyl diphenylmethane dicarbamates, diethyl diphenylmethane dicarbamates, dipropyl diphenylmethane dicarbamates.

Suitable hydroxyl compounds include aliphatic or aromatic, cyclic or alicyclic alcohols such as, for example, methanol, ethanol, n-propanol, isopropanol, pentanol, hexanol, 3,3-dimethyl-2-butanol, 2-propanol, N,N-dimethylethanolamine, 1-methoxy-2-propanol, 2-methoxyethanol, 1-ethoxycyclo-propanol, 2-isopropoxyethanol, 1,3-dimethoxy-2-propanol, 1,1-dimethoxy-ethanol, 2-methoxy-1-propanol, 2-methoxy-3-propanol, dimethyloxime, 1,3-dimethoxy-2-propanol, benzyl alcohol, phenol, hydroxylamines, halogenated alcohols such as hexafluoroisopropanol or trifluoroethanol, halogenated phenols such as ortho-chlorophenol, para-chlorophenol, ortho-fluorophenol, para-fluorophenol and the like.

An essential constituent of the catalyst composition employed according to the invention is one of the Group VIII-B metals, preferably palladium, or a compound thereof.

Thus, palladium black or elemental palladium deposited on zeolite, carbon and oxide supports such as alumina, silica are suitable, as well as palladium compounds such as halides, and complexes with such compounds as carbon monoxide, amines, phosphines and olefins. The catalytic material also contains a halogenide source, preferably an iodide source. It may be an alkali metal iodide or alkyl iodide.

Carbon monoxide employed in the process of the present invention may be pure gaseous carbon monoxide, but may also contain impurities such as nitrogen and carbon dioxide. An impurity content of less than 10% v/v does not affect the reaction pattern and from industrial viewpoint, it may be advantageous to use carbon monoxide with small amounts of impurities. Carbon monoxide is employed in an amount of at least 1 mole per amino group of the polymeric amine compound. A more preferred amount of carbon monoxide is from 2 to 100 moles per amino group of the polymeric amine compound.

The oxidising agent used in the process of the invention may be pure oxygen, a gas containing oxygen such as air or an organic nitro compound or a mixture thereof. Oxygen however is preferred. The process also tolerates the employment in some cases of an oxygen containing gas, which additionally contains other non-interfering gases, such as argon, nitrogen or carbon dioxide.

The organic hydroxyl compound, which forms one of the reactants, can also function as a solvent. However, where necessary, other solvents, which do not affect the reaction adversely (i.e. inert solvents), may also be used. Exemplary of such solvents are aromatic hydrocarbons such as benzene, toluene, xylene, monochlorobenzene, ortho-dichlorobenzene, and nitriles such as acetonitrile and benzonitrile, ethers such as tetrahydrofuran and 2-dioxan, ketones such as acetone and methyl ethyl ketone, amides such as N,N' dimethyl formamide and N,N' dimethyl acetamide and esters such as ethyl acetate and ethyl benzoate.

The component of the catalyst that acts as a precursor can comprise a soluble compound of a transition metal (Group VIII-B) supported on a suitable carrier. Of the transition metals, palladium is especially preferred. Specific examples of the catalyst precursors include Palladium black, supported palladium catalysts such as Pd/C, Pd/Al$_2$O$_3$, Pd/ZSM5, Pd/CaCO$_3$ and the like. Pd black, which has been prepared by various reducing agents, such as hydrazine hydrate, sodium formate, formaldehyde, sodium borohydride, LiAlH$_4$, and H$_2$, can be used.

Soluble Pd compounds that can be used are: PdCl$_2$, PdBr$_2$, Pd(NO$_3$)$_2$, Pd(OAc)$_2$, Pd oxalate, [Pd(NH$_3$)$_4$]X$_2$, PdL$_2$X, Pd(CO)X, wherein X is Cl, Br or I, and L is triphenyl phosphine, pyridine, isoquinoline, tributyl phosphine, benzonitrile and the like.

The halogen-containing promoter can be selected from alkali metal halides, alkaline earth metal halides, quaternary ammonium halides, oxo acids of halogen atom and their salts, and complexes containing halogen ions, organic halides and halogen molecules. However, of all the halogen compounds, which act as promoters, those compounds containing iodine are particularly preferred. These include KI, NaI, LiI, CsI, tetrabutyl ammonium iodide, iodine and the like.

The oxidative carbonylation reaction of the present invention can be carried out in a temperature range of 80–350° C., more preferably between 120–250° C. However, it has been found that temperature is an important factor in obtaining a good yield of carbamate derivatives. The carbonylation is carried out under a CO partial pressure of about 5–6000 psig, more preferably between 100–1500 psig. The partial pressure of O$_2$ is employed between 5–1000 psig, more preferably between 10–300 psig. The ratio of CO to O$_2$ used in this process is an important factor and activity and selectivity of the catalyst was found to be drastically affected if the CO to O$_2$ ratio was varied. The ratio of CO to O$_2$ in the reactor can be in the range of 1:1 to 50:1, preferably in the range of 5:1 to 20:1.

In giving effect to the reaction of the present invention, it has been found convenient to employ 1 mole of catalyst per 5–8000 moles of amine functionality. More preferred range comprises 1 mole of catalyst per 100–500 moles of amine functionality. The ratio of iodide promoter to metal is in the range of about 0.1 to 50, and more preferably between 0.5 to 15.

The amount of organic hydroxyl compound employed is at least 1 mole per amine group of polymeric amine compound. However, it is more preferable to use 3–100 moles of the hydroxyl group per amino group of polymeric amine compound.

The invention will now be described in detail in the following examples, which should not however be considered to limit the scope of the invention.

EXAMPLES

Example 1

Polymeric methylene diphenyl urethane was prepared by charging the following components into a 50 ml high-pressure stirred autoclave:

| | |
|---|---|
| polymeric DADPM | 0.8 g |
| Pd-ZSM-5(10%) | 0.08 g |
| Sodium iodide (NaI) | 0.008 g |
| and excess of ethyl alcohol. | 20 ml |

The autoclave was sealed, flushed twice with carbon monoxide, pressurised with 744 psig of carbon monoxide and 56 psig of oxygen resulting in a total pressure of 800 psig at room temperature. The reaction was carried out at 190° C. (1000 psig) for two hours with constant vigorous stirring. The progress of the reaction was monitored by recording the pressure drop, and the gases were repressurised in a 2:1 ratio of carbon monoxide to oxygen as necessary. After 2 hr., the reactor was cooled and discharged. The liquid portion was filtered from the insoluble material. The solvent ethyl alcohol was evaporated completely under vacuum. A sticky solid product, weighing about 1.09 g was thus obtained. The product was analysed by IR, $^1$H and $^{13}$C NMR and proved to be more than 95% pure which results in an estimated yield of 75–80%.

Example 2

The procedure of Example 1 was repeated except that the reactor used was 300 ml instead of 50 ml. The following components were charged to the reactor:

| | |
|---|---|
| polymeric DADPM | 6.4 g |
| Pd-ZSM-5(10%) | 0.64 g |
| Sodium iodide (NaI) | 0.064 g |
| and excess of ethyl alcohol. | |

The yield obtained of the sticky solid product was about 10.6 g. Estimated yield of carbamate based on weight and $^{13}C$ NMR analysis is 75–80%. About 20% of unreacted aromatic amine functions were observed.

Example 3

The procedure of Example 1 was repeated except that the catalyst 1% Pd-ZSM-% was employed instead of 10% Pd-ZSM-%. The components charged were:

| | |
|---|---|
| polymeric DADPM | 0.8 g |
| Pd-ZSM-5(1%) | 0.08 g |
| Sodium iodide (NaI) | 0.008 g |
| and excess of ethyl alcohol. | |

An insoluble residue of about 0.44 g was obtained together with a soluble fraction which based on $^{13}C$ NMR proved to be pure carbamate.

Example 4

The procedure of Example 1 was repeated except that the catalyst Pd metal was employed instead of 10%Pd-ZSM-5. The components charged were:

| | |
|---|---|
| polymeric DADPM | 0.8 g |
| Pd-metal | 0.004 g |
| Sodium iodide (NaI) | 0.008 g |
| and excess of ethyl alcohol. | |

An insoluble residue of about 0.44 g was obtained together with a soluble fraction which based on $^{13}C$ NMR proved to contain carbamate.

Example 5

The procedure of Example 1 was repeated except that the catalyst Pd acetate was employed instead of 10%Pd-ZSM-5. The components charged were:

| | |
|---|---|
| polymeric DADPM | 0.8 g |
| Pd(OAc)$_2$ | 0.008 g |
| Sodium iodide (NaI) | 0.008 g |
| and excess of ethyl alcohol. | |

An insoluble residue of about 0.02 g was obtained together with a soluble fraction which based on $^{13}C$ NMR proved to contain carbamate.

Comparative Example 1

The procedure of Example 1 was repeated except that 4,4' DADPM was used instead of polymeric DADPM as the starting compound. An insoluble residue of 0.12 g was obtained together with a soluble fraction containing 61% 4,4' diethyl carbamate and 2.4% 4-amino-4'-ethylcarbonylamino-diphenyl methane (monocarbamate), both measured by HPLC.

Comparative Example 2

The procedure of Example 2 was repeated except that the amount of start material used was halved and that 4,4' DADPM was used instead of polymeric DADPM as the starting compound. An insoluble residue of 1.12 g was obtained together with a soluble fraction containing 49.4% 4,4' diethyl carbamate and 2.4% 4-amino-4'-ethylcarbonylamino-diphenyl methane (monocarbamate), both measured by HPLC.

Comparative Example 3

The procedure of Example 3 was repeated except that 4,4' DADPM was used instead of polymeric DADPM as the starting compound. An insoluble residue of 0.106 g was obtained together with a soluble fraction containing 49.5% 4,4' diethyl carbamate and 7.92% 4-amino-4'-ethylcarbonylamino-diphenyl methane (monocarbamate), both measured by HPLC.

Comparative Example 4

The procedure of Example 4 was repeated except that 4,4' DADPM was used instead of polymeric DADPM as the starting compound and that the reaction temperature was 170° C. An insoluble residue of 0.32 g was obtained together with a soluble fraction containing 24.1% 4,4' diethyl carbamate and 6.4% 4-amino-4'-ethylcarbonylamino-diphenyl methane (monocarbamate), both measured by HPLC.

Comparative Example 5

The procedure of Example 5 was repeated except that 4,4' DADPM was used instead of polymeric DADPM as the starting compound. An insoluble residue of 0.05 g was obtained together with a soluble fraction containing 52.3% 4,4'diethyl carbamate and 2.7% 4-amino-4'-ethylcarbonylamino-diphenyl methane (monocarbamate), both measured by HPLC.

What is claimed is:

1. A method for preparing a polymeric carbamate compound which comprises the step of reacting polymeric diaminodiphenylmethane with carbon monoxide, an oxidising agent, and an organic hydroxyl compound in the presence of a catalyst system comprising:
    (a) a precursor containing a Group VIII or lanthanide metal, and
    (b) at least one halogen containing promoter effective to promote said reacting.
2. The method of claim 1, wherein the Group VIII or lanthanide metal is palladium or cerium.
3. The method of claim 1, wherein the precursor is selected from the group consisting of Pd black, Pd/C, Pd/Al$_2$O$_3$, Pd/CaCO$_3$, Pd/ZSM5, PdCl$_2$, PdBr$_2$, PdI$_2$, Pd(NO$_3$)$_2$, Pd(OAc)$_2$, Pd oxalate, [Pd(NH$_3$)$_4$]X$_2$, PdL$_2$X, and Pd(CO)X, wherein X is Cl, Br or I.
4. The method of claim 2, wherein the precursor is selected from the group consisting of Pd black, Pd/C, Pd/Al$_2$O$_3$, Pd/CaCO$_3$, Pd/ZSM5, PdCl$_2$, PdBr$_2$, PdI$_2$, Pd(NO$_3$)$_2$, Pd(OAc)$_2$, Pd oxalate, [Pd(NH$_3$)$_4$]X$_2$, PdL$_2$X, and Pd(CO)X, wherein X is Cl, Br or I.
5. The method of claim 1, wherein the oxidising agent is oxygen or air.
6. The method of claim 1, wherein the halogen containing promoter contains iodine.

7. The method of claim 6, wherein the halogen containing promoter is selected from the group consisting of NaI, LiI, CsI, tetra butyl ammonium iodide, tetra heptyl ammonium iodide, and iodine.

8. The method of claim 1, wherein the ratio of the halogen containing promoter to the precursor is in the range of about 0.5–15.

9. The method of claim 1, wherein said reacting is conducted at a temperature of about 100° C. to about 300° C.

10. The method of claim 1, wherein said reacting is conducted at a pressure of about 10 bar to about 100 bar.

11. The method of claim 9, wherein said reacting is conducted at a pressure of about 10 bar to about 100 bar.

12. The method of claim 10, wherein the reaction is effected in the absence of an inert solvent.

13. The method of claim 11, wherein the reaction is effected in the absence of an inert solvent.

14. The method of claim 10, wherein the reaction is effected in the presence of an inert solvent.

15. The method of claim 11, wherein the reaction is effected in the presence of an inert solvent.

16. The method of claim 15, wherein said inert solvent is selected from the group consisting of aromatic hydrocarbons, nitriles, ethers, ketones, amides, and esters.

17. The method of claim 1, wherein oxygen is present during said reacting and the $CO:O_2$ ratio in the range of about 5:1 to about 20:1.

18. A method for preparing a polymeric carbamate compound which comprises the step of reacting polymeric diaminodiphenylmethane with carbon monoxide, an oxidising agent, and an organic hydroxyl compound in the presence of a catalyst system comprising:
    (a) a precursor containing palladium, and
    (b) at least one halogen containing promoter effective to promote the said reacting.

19. The method of claim 18, wherein the oxidising agent is oxygen or air.

20. The method of claim 19, wherein the halogen containing promoter is selected from the group consisting of NaI, LiI, CsI, tetra butyl ammonium iodide, tetra heptyl ammonium iodide, and iodine.

21. The method of claim 20, wherein said reacting is conducted at a temperature of about 100° C. to about 300° C.

22. The method of claim 21, wherein said reacting is conducted at a pressure of about 10 bar to about 100 bar.

23. The method of claim 22, wherein the reaction is effected in the absence of an inert solvent.

24. The method of claim 22, wherein the reaction is effected in the presence of an inert solvent.

25. The method of claim 24, wherein the inert solvent is selected from the group consisting of aromatic hydrocarbons, nitriles, ethers, ketones, amides, and esters.

26. The method of claim 23, wherein oxygen is present during said reacting and the partial pressure ratio of $CO:O_2$ is in the range of about 5:1 to about 20:1.

27. The method of claim 25, wherein oxygen is present during said reacting and the partial pressure ratio of $CO:O_2$ is in the range of about 5:1 to about 20:1.

28. A method for preparing a polymeric carbamate compound which comprises the step of reacting polymeric diaminodiphenylmethane with:
    (a) carbon monoxide,
    (b) an oxidising agent selected from the group consisting of oxygen and air, and
    (c) an organic hydroxyl compound in the presence of a catalyst system comprising:
    (a) a precursor containing palladium, and
    (b) at least one halogen containing promoter effective to promote said reacting, wherein the halogen containing promoter is selected from the group consisting of NaI, LiI, CsI, tetra butyl ammonium iodide, tetra heptyl ammonium iodide, and iodine.

29. The method of claim 28, wherein said reacting is conducted at a temperature of about 100° C. to about 300° C.

30. The method of claim 28, wherein said reacting is conducted at a pressure of about 10 bar to about 100 bar.

31. The method of claim 28, wherein the reaction is effected in the absence of an inert solvent.

32. The method of claim 28, wherein the reaction is effected in the presence of an inert solvent.

33. The method of claim 32, wherein the inert solvent is selected from the group consisting of aromatic hydrocarbons, nitriles, ethers, ketones, amides, and esters.

34. The method of claim 28, wherein oxygen is present during said reacting and the partial pressure ratio of $CO:O_2$ is in the range of about 5:1 to about 20:1.

* * * * *